United States Patent
Katakura (10) Patent No.: US 10,845,586 B2
(45) Date of Patent: Nov. 24, 2020

(54) ENDOSCOPE OPTICAL SYSTEM

(71) Applicant: OLYMPUS CORPORATION, Hachioji (JP)

(72) Inventor: Masahiro Katakura, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 136 days.

(21) Appl. No.: 16/176,886

(22) Filed: Oct. 31, 2018

(65) Prior Publication Data
US 2019/0064501 A1 Feb. 28, 2019

Related U.S. Application Data

(63) Continuation of application No. PCT/JP2017/023494, filed on Jun. 27, 2017.

(30) Foreign Application Priority Data

Jul. 4, 2016 (JP) ................. 2016-132639

(51) Int. Cl.
*G02B 23/24* (2006.01)
*G02B 13/04* (2006.01)
(Continued)

(52) U.S. Cl.
CPC ........ *G02B 23/243* (2013.01); *A61B 1/00096* (2013.01); *A61B 1/00188* (2013.01); (Continued)

(58) Field of Classification Search
CPC ...... G02B 21/02; G02B 21/33; G02B 23/243; G02B 9/12; G02B 13/003; G02B 1/041; (Continued)

(56) References Cited

U.S. PATENT DOCUMENTS

2011/0043664 A1  2/2011 Mihara
2012/0057251 A1  3/2012 Takato
(Continued)

FOREIGN PATENT DOCUMENTS

EP  3037858 A1 * 6/2016  .......... G02B 15/173
JP  2009265569 A  11/2009
(Continued)

OTHER PUBLICATIONS

International Search Report (ISR) dated Sep. 19, 2017 issued in International Application No. PCT/JP2017/023494.
(Continued)

*Primary Examiner* — William R Alexander
*Assistant Examiner* — Sharrief I Broome
(74) *Attorney, Agent, or Firm* — Holtz, Holtz & Volek PC

(57) ABSTRACT

The endoscope optical system includes in order from an object side, a first lens group having a negative refractive power, a second lens group having a positive refractive power, and a third lens group having a positive refractive power. Switching between a normal observation and a magnified observation is possible by fixing the first lens group and the third lens group, and moving the second lens group. The third lens group includes a cemented lens. The cemented lens includes an object-side lens and an image-side lens, and the following conditional expressions (1) and (2) are satisfied:

$$0.471 < nd02 - nd01 < 0.475 \quad (1)$$

$$52.6 < vd01 - vd02 < 53 \quad (2).$$

14 Claims, 5 Drawing Sheets

(51) Int. Cl.
    *A61B 1/00*     (2006.01)
    *A61B 1/04*     (2006.01)
    *A61B 1/06*     (2006.01)
    *G02B 9/12*     (2006.01)

(52) U.S. Cl.
    CPC .......... *G02B 13/04* (2013.01); *A61B 1/00183* (2013.01); *A61B 1/00186* (2013.01); *A61B 1/04* (2013.01); *A61B 1/0638* (2013.01); *G02B 9/12* (2013.01); *G02B 23/2484* (2013.01)

(58) Field of Classification Search
    CPC .......... G02B 3/00; G02B 7/008; G02B 7/028; G02B 21/025; G02B 13/04; G02B 13/18; G02B 15/177; G02B 21/22; G02B 3/02; G02B 9/10; G02B 9/34; G02B 13/0025; G02B 13/006; G02B 13/02; H01L 2924/00; H01L 2924/12033; H01L 2924/12041; H01L 2924/12042; H01L 2924/12043; H01L 2924/14; H01L 2924/181; H01L 27/14625; H01L 2224/16225; H01L 2224/16245; H01L 24/50; H01L 25/0756; H01L 25/13; H01L 2924/1815; H01L 2924/3011; H01L 31/02325; H01L 33/58; H01L 33/60; H01L 21/32135; H01L 21/67069; G11B 7/1374; G11B 2007/13727; G11B 7/13922; G11B 7/1387; G11B 2007/0006; G11B 7/122; G11B 7/1353; G11B 7/1378; G11B 2007/0013; G11B 7/121; G11B 7/1275; G11B 7/1367; G11B 7/1369; G11B 7/1376; G11B 7/1392; G11B 7/13925; G11B 7/22

See application file for complete search history.

(56) References Cited

U.S. PATENT DOCUMENTS

| | | | |
|---|---|---|---|
| 2015/0268460 A1* | 9/2015 | Takada ............... | G02B 23/2438 359/738 |
| 2016/0154230 A1* | 6/2016 | Katakura ............. | G02B 15/177 359/690 |
| 2017/0038570 A1 | 2/2017 | Takato | |
| 2017/0071449 A1* | 3/2017 | Noguchi ................. | G02B 7/04 |
| 2017/0090151 A1* | 3/2017 | Naruse ................... | G02B 13/04 |
| 2017/0343790 A1* | 11/2017 | Ushio ..................... | G02B 9/34 |

FOREIGN PATENT DOCUMENTS

| | | |
|---|---|---|
| WO | 2011070930 A1 | 6/2011 |
| WO | 2015025843 A1 | 2/2015 |
| WO | 2016084494 A1 | 6/2016 |

OTHER PUBLICATIONS

Written Opinion dated Sep. 19, 2017 issued in International Application No. PCT/JP2017/023494.

International Preliminary Report on Patentability (IPRP) (and English language translation thereof) and Written Opinion dated Jan. 17, 2019 issued in International Application No. PCT/JP2017/023494.

\* cited by examiner

ENDOSCOPE OPTICAL SYSTEM

CROSS-REFERENCE TO RELATED APPLICATION

The present application is a continuation application of PCT/JP2017/023494 filed on Jun. 27, 2017 which is based upon and claims the benefit of priority from Japanese Patent Application No. 2016-132639 filed on Jul. 4, 2016; the entire contents of which are incorporated herein by reference.

BACKGROUND OF THE INVENTION

Field of the Invention

The present invention relates to an endoscope optical system.

Description of the Related Art

An objective optical system described in International Unexamined Patent Application Publication No. 2011/070930 is available as an objective optical system for endoscope. The objective optical system includes in order from an object side, a first lens group having a negative refractive power, a second lens group having a positive refractive power, and a third lens group having a positive refractive power.

In this objective optical system, the second lens group moves along an optical axis and switching from a normal observation to a magnified observation is carried out.

SUMMARY OF THE INVENTION

An endoscope optical system according to at least some embodiments of the present invention comprises in order from an object side, a first lens group having a negative refractive power,
a second lens group having a positive refractive power, and
a third lens group having a positive refractive power, wherein switching between a normal observation and a magnified observation is possible by fixing the first lens group and the third lens group, and moving the second lens group, and the third lens group includes a cemented lens, and the cemented lens includes an object-side lens and an image-side lens, and the following conditional expressions (1) and (2) are satisfied:

$$0.471 < nd02 - nd01 < 0.475 \quad (1)$$

$$52.6 < vd01 - vd02 < 53 \quad (2)$$

where, nd01 denotes a refractive index of the object-side lens for a d-line, nd02 denotes a refractive index of the image-side lens for the d-line, vd01 denotes Abbe number for the object-side lens for the d-line, and vd02 denotes Abbe number for the image-side lens for the d-line.

DETAILED DESCRIPTION OF THE INVENTION

Reasons for and an effect of adopting such arrangements for an endoscope optical system according to the present embodiment will be described below by using the accompanying diagrams. However, the present invention is not restricted to the embodiment described below.

An endoscope optical system according to the present embodiment, in endoscopic observation, enables to carry out a normal observation and a magnified observation with one optical system. For this, the endoscope optical system includes a plurality of lens groups, and at least one lens group out of the plurality of lens groups moves on an optical axis. Accordingly, it is possible to carry out the normal observation when focused to an object point at a long distance, and to carry out the magnified observation when focused to an object point at a close distance.

Figure 1A:
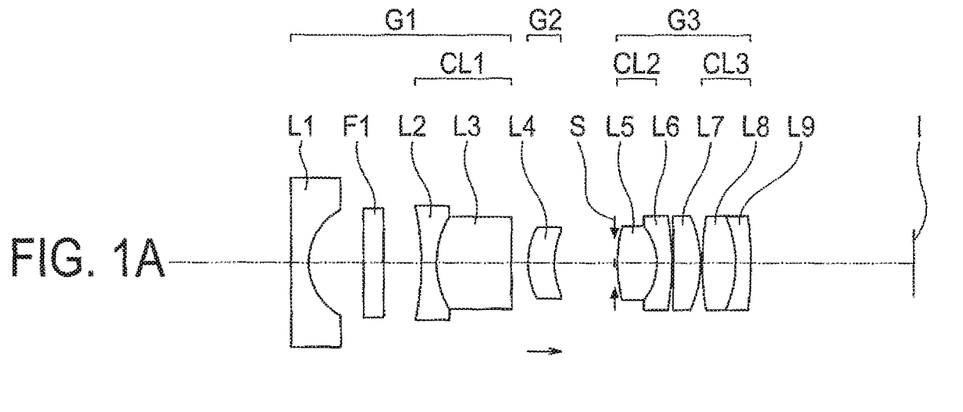
FIG. 1A and FIG. 1B are cross-sectional views showing a specific arrangement of an endoscope optical system according to the present embodiment.
Figure 1B:
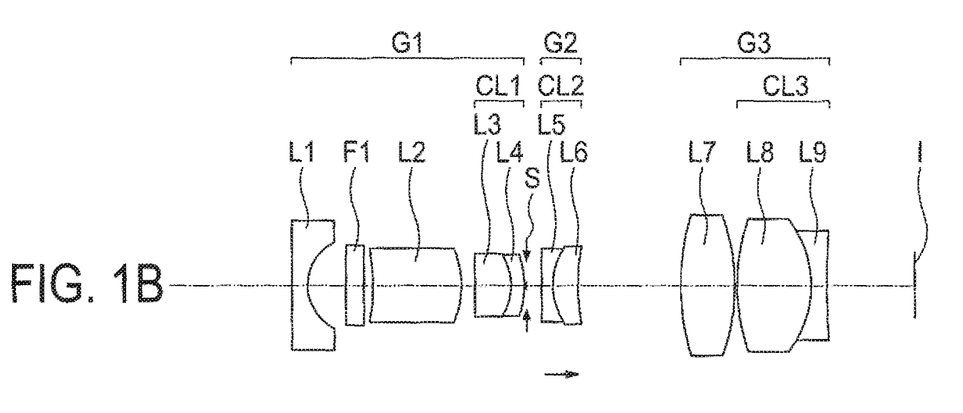

The endoscope optical system of the present embodiment will be described below. FIG. 1A and FIG. 1B are diagrams showing the endoscope optical system of the present embodiment. FIG. 1A is a diagram showing an endoscope optical system according to a first embodiment and FIG. 1B is a diagram showing an endoscope optical system according to a second embodiment.

The endoscope optical system according to the first embodiment includes in order from an object side, a first lens group having a negative refractive power, a second lens group having a positive refractive power, and a third lens group having a positive refractive power, wherein switching between the normal observation and the magnified observation is possible by fixing the first lens group and the third lens group, and moving the second lens group, and the third lens group includes a cemented lens, and the cemented lens includes an object-side lens and an image-side lens, and the following conditional expressions (1) and (2) are satisfied:

$$0.471 < nd02 - nd01 < 0.475 \quad (1)$$

$$52.6 < vd01 - vd02 < 53 \quad (2)$$

where, nd01 denotes a refractive index of the object-side lens for a d-line, nd02 denotes a refractive index of the image-side lens for the d-line, vd01 denotes Abbe number for the object-side lens for the d-line, and vd02 denotes Abbe number for the image-side lens for the d-line.

As shown in FIG. 1A, the endoscope optical system of the first embodiment includes in order from the object side, a first lens group G1 having a negative refractive power, a second lens group G2 having a positive refractive power, and a third lens group G3 having a positive refractive power.

In an endoscope optical system, the optical system is sought to be provided with a focusing function while having an appropriate back focus. In order to fulfill this requirement, in the endoscope optical system of the first embodiment, an optical system includes three lens groups, and furthermore, a refractive power of the three lens groups is made to be a negative refractive power, a positive refractive power, and a positive refractive power in order from the object side. Accordingly, it is possible to secure a long back focus.

Various errors occur at the time of manufacturing. By adopting the abovementioned arrangement, it is possible to make small an amount of change in an aberration with respect to an error of a predetermined amount. Consequently, it is possible to realize an endoscope optical system having a high imaging performance while simplifying an adjustment work at the time of manufacturing.

The first lens group G1 includes a negative lens L1, a negative lens L2, and a positive lens L3. The negative lens L2 and the positive lens L3 form a cemented lens CL1.

The second lens group G2 includes a positive lens L4.

The third lens group G3 includes a positive lens L5, a negative lens L6, a positive lens L7, a positive lens L8, and a negative lens L9. The positive lens L5 and the negative lens L6 form a cemented lens CL2. The positive lens L8 and the negative lens L9 form a cemented lens CL3.

Switching between the normal observation and the magnified observation is made possible by moving the second lens group G2. At the time of moving the second lens group G2, both the first lens group G1 and the third lens group G3 are fixed. At the time of switching from the normal observation to the magnified observation, the second lens group G2 moves toward an image side.

An observation distance differs for the normal observation and the magnified observation. Therefore, focusing is also carried out at the time of switching between the normal observation and the magnified observation. In the endoscope optical system of the first embodiment, focusing is carried out by moving the second lens group G2.

In the endoscope optical system of the first embodiment, it is possible to distribute the positive refractive power between the second lens group G2 and the third lens group G3. Accordingly, it is possible to lessen an aberration fluctuation at the time of focusing.

The third lens group G3 includes the cemented lens. The cemented lens includes the object-side lens and the image-side lens. It is possible to correct the chromatic aberration by the object-side lens and the image-side lens.

In the arrangement shown in FIG. 1A, the positive lens L8 in the cemented lens CL3 is the object-side lens, and the negative lens L9 in the cemented lens CL3 is the image-side lens. Since the cemented lens CL3 includes a positive lens and a negative lens, it is possible to correct the chromatic aberration favorably.

A plane parallel plate F1 is disposed between the negative lens L1 and the negative lens L2. It is possible to dispose the plane parallel plate F1 at an arbitrary position in the endoscope optical system.

An aperture stop S is disposed between the second lens group G2 and the third lens group G3. More specifically, the aperture stop S is positioned near an object-side surface of the positive lens L5.

The endoscope optical system according to the first embodiment has the abovementioned arrangement, and conditional expressions (1) and (2) are satisfied.

As mentioned above, the third lens group includes the cemented lens. Conditional expressions (1) and (2) are conditional expressions related optical characteristics of the cemented lens.

Conditional expression (1) is a conditional expression in which a difference between a refractive index of the object-side lens and a refractive index of the image-side lens is indicated. By satisfying conditional expression (1), it is possible to make the difference between the refractive index of the object-side lens and the refractive index of the image-side lens appropriate. As a result, it is possible to correct a longitudinal chromatic aberration and a chromatic aberration of magnification favorably.

In a case of exceeding an upper limit value of conditional expression (1), an availability of glass material is lowered. Therefore, it is not preferable to exceed the upper limit value of conditional expression (1).

In a case of falling below a lower limit value of conditional expression (1), the difference between the refractive index of the object-side lens and the refractive index of the image-side lens becomes excessively small. In this case, for correcting the longitudinal chromatic aberration and the chromatic aberration of magnification favorably, a curvature of a lens surface of the cemented lens is to be made extremely large. However, as the curvature of the lens surface becomes large, an amount of other aberrations that occur increases. Therefore, it is not preferable to fall below the lower limit value of conditional expression (1).

Conditional expression (2) is a conditional expression in which a difference between Abbe number for the object-side lens and Abbe number for the image-side lens is indicated. By satisfying conditional expression (2), it is possible to make the difference between the Abbe number for the object-side lens and the Abbe number for the image-side lens appropriate. As a result, it is possible to correct the longitudinal chromatic aberration and the chromatic aberration of magnification favorably.

In a case of exceeding an upper limit value of conditional expression (2), the availability and workability of glass material are lowered. Therefore, is not preferable to exceed the upper limit value of conditional expression (2).

In a case of falling below a lower limit value of conditional expression (2), the difference between the Abbe number for the object-side lens and the Abbe number for the image-side lens becomes excessively small. Consequently, it is not possible to correct both the longitudinal chromatic aberration and the chromatic aberration of magnification favorably. Therefore, it is not preferable to fall below the lower limit value of conditional expression (2).

The endoscope optical system according to the second embodiment includes in order from an object side, a first lens group having a positive refractive power, a second lens group having a negative refractive power, and a third lens group having a positive refractive power, wherein switching between the normal observation and the magnified observation is possible by fixing the first lens group and the third lens group, and moving the second lens group, and the third lens group includes a cemented lens, and the cemented lens includes an object-side lens and an image-side lens, and the following conditional expressions (1) and (2) are satisfied:

$$0.471 < nd02 - nd01 < 0.475 \quad (1)$$

$$52.6 < vd01 - vd02 < 53 \quad (2)$$

where, $nd01$ denotes a refractive index of the object-side lens for a d-line, $nd02$ denotes a refractive index of the image-side lens for a d-line, $vd01$ denotes Abbe number for the object-side lens for a d-line, and vd02 denotes Abbe number for the image-side lens for a d-line.

As shown in FIG. 1B, the endoscope optical system of the second embodiment includes in order from the object side, a first lens group G1 having a positive refractive power, a second lens group G2 having a negative refractive power, and a third lens group G3 having a positive refractive power.

In an endoscope optical system, the optical system is sought to be provided with a focusing function while small-sizing the optical system. In order to fulfill this requirement, in the endoscope optical system of the second embodiment, an optical system includes three lens groups, and furthermore, a refractive power of the three lens groups is made to be a positive refractive power, a negative refractive power, and a positive refractive power, in order from the object side. Accordingly, it is possible to reduce the number of lenses in each group. As a result, small-sizing of the optical system and cost reduction are possible.

The first lens group G1 includes a negative lens L1, a positive lens L2, a positive lens L3, and a negative lens L4. The positive lens L3 and the negative lens L4 form a cemented lens CL1.

The second lens group G2 includes a negative lens L5 and a positive lens L6. The negative lens L5 and the positive lens L6 form a cemented lens CL2.

The third lens group G3 includes a positive lens L7, a positive lens L8, and a negative lens L9. The positive lens L8 and the negative lens L9 form a cemented lens CL3.

Switching between the normal observation and the magnified observation is made possible by moving the second lens group G2. At the time of moving the second lens group G2, both the first lens group G1 and the third lens group G3 are fixed. At the time of switching from the normal observation to the magnified observation, the second lens group G2 moves toward an image side.

In the endoscope optical system of the second embodiment, it is possible to distribute the positive refractive power between the first lens group G1 and the third lens group G3. Accordingly, it is possible to lessen an aberration fluctuation at the time of focusing.

The third lens group G3 includes the cemented lens. The cemented lens includes the object-side lens and the image side lens. It is possible to correct the chromatic aberration by the object-side lens and the image-side lens.

In an arrangement shown in FIG. 1B, the positive lens L8 in the cemented lens CL3 is the object-side lens and the negative lens L9 in the cemented lens CL3 is the image-side lens. Since the cemented lens CL3 includes a positive lens and a negative lens, it is possible to correct the chromatic aberration favorably.

A plane parallel plate F1 is disposed between the negative lens L1 and the positive lens L2. It is possible to dispose the plane parallel plate F1 at an arbitrary position in the endoscope optical system.

An aperture stop S is disposed between the first lens group G1 and the second lens group G2. More specifically, the aperture stop S is positioned near an image-side surface of the negative lens L4.

The endoscope optical system according to the second embodiment has the abovementioned arrangement, and conditional expressions (1) and (2) are satisfied.

A technical significance of conditional expressions (1) and (2) has already been described. Therefore, the description of the technical significance of conditional expressions (1) and (2) is omitted here.

In the endoscope optical system according to the first embodiment and the endoscope optical system according to the second embodiment (hereinafter, referred to as the 'endoscope optical system according to the present embodiment'), it is preferable that the following conditional expression (3) be satisfied:

$$0.05 < (nd02 - nd01)/fno < 0.2 \quad (3)$$

where, nd01 denotes the refractive index of the object-side lens for the d-line, nd02 denotes the refractive index of the image-side lens for the d-line, and fno denotes an F-number of the endoscope optical system at the time of the normal observation.

Conditional expression (3) is a conditional expression in which a ratio of a difference between a refractive index of the cemented lens and the F-number of the endoscope optical system is indicated. By satisfying conditional expression (3), it is possible to make both the F-number of the endoscope optical system and the difference in the refractive index of the cemented lens appropriate. Consequently, it is possible to realize an endoscope optical system which is bright and which has a lesser chromatic aberration.

In a case of falling below a lower limit value of conditional expression (3), the difference in the refractive index of the cemented lens becomes excessively small. Consequently, it is not possible to correct the chromatic aberration favorably. Therefore, it is not preferable to fall below the lower limit value of conditional expression (3).

In a case of exceeding an upper limit value of conditional expression (3), the F-number becomes excessively small. Consequently, correction of an axial aberration and correction of an off-axis aberration become difficult. Therefore, is not preferable to exceed the upper limit value of conditional expression (3).

It is more preferable that the following conditional expression (3') be satisfied instead of conditional expression (3).

$$0.1 < (nd02 - nd01)/fno < 0.15 \quad (3')$$

It is even more preferable that the following conditional expression (3") be satisfied instead of conditional expression (3).

$$0.13 < (nd02 - nd01)/fno < 0.14 \quad (3'')$$

In the endoscope optical system according to the present embodiment, it is preferable that the first lens group include a negative lens which is nearest to object, and the following conditional expressions (4) and (5) be satisfied:

$$0.76 < nd01/ndA < 0.81 \quad (4)$$

$$1.02 < nd02/ndA < 1.07 \quad (5)$$

where, nd01 denotes the refractive index of the object-side lens for the d-line, nd02 denotes the refractive index of the image-side lens for the d-line, and ndA denotes a refractive index of the negative lens for the d-line.

In the endoscope optical system according to the present embodiment, the first lens group includes the negative lens which is disposed nearest to object (hereinafter, referred to as the 'negative lens'). Conditional expression (4) is a conditional expression in which a ratio of the refractive index of the negative lens and the refractive index of the object-side lens is indicated. Conditional expression (5) is a conditional expression in which a ratio of the refractive index of the negative lens and the refractive index of the image-side lens is indicated.

By satisfying conditional expressions (4) and (5), it is possible to make each of the refractive index of the negative lens, the refractive index of the object-side lens, and the refractive index of the image-side lens appropriate. As a result, in each of the negative lens and the cemented lens, it is possible to make a shape of a lens surface to have a favorable workability.

In a case of either falling below a lower limit value of conditional expression (4) or falling below a lower limit value of conditional expression (5), the refractive index of the negative lens becomes excessively high. Consequently, an availability of glass material is lowered remarkably. Therefore, it is not preferable to fall below the lower limit value of conditional expression (4) and the lower limit value of conditional expression (5).

In a case of either exceeding an upper limit value of conditional expression (4) or exceeding an upper limit value of conditional expression (5), the refractive index of the negative lens becomes excessively small. Consequently, a curvature of the negative lens is made extremely large. When the curvature of the negative lens is made excessively large, the workability of the negative lens is degraded. Therefore, it is not preferable to exceed the upper limit value of conditional expression (4) and the upper limit value of conditional expression (5).

It is more preferable that the following conditional expression (4') be satisfied instead of conditional expression (4).

$$0.77 < nd01/ndA < 0.80 \quad (4')$$

It is even more preferable that the following conditional expression (4") be satisfied instead of conditional expression (4).

$$0.78 < nd01/ndA < 0.79 \quad (4")$$

It is more preferable that the following conditional expression (5') be satisfied instead of conditional expression (5).

$$1.03 < nd02/ndA < 1.06 \quad (5')$$

It is even more preferable that the following conditional expression (5") be satisfied instead of conditional expression (5).

$$1.04 < nd02/ndA < 1.05 \quad (5")$$

In the endoscope optical system of the present embodiment, it is preferable that the first lens group have a negative lens which is nearest to object, and the following conditional expressions (6) and (7) be satisfied:

$$0 \leq |RCEM/RAf| < 0.03 \quad (6)$$

$$-5 < RCEM/RAr < -0.5 \quad (7)$$

where,

RAf denotes a radius of curvature of an object-side surface of the negative lens, RAr denotes a radius of curvature of an image-side surface of the negative lens, and RCEM denotes a radius of curvature of a cemented surface of the cemented lens.

Conditional expression (6) is a conditional expression in which a ratio of the radius of curvature of the cemented surface of the cemented lens and the radius of curvature of the object-side surface of the negative lens is indicated. Conditional expression (7) is a conditional expression in which a ratio of the radius of curvature of the cemented surface of the cemented lens and the radius of curvature of the image-side surface of the negative lens is indicated.

By satisfying conditional expressions (6) and (7), it is possible to make appropriate each of the radius of curvature of the cemented surface of the cemented lens, the radius of curvature of the object-side surface of the negative lens, and the radius of curvature of the image-side surface of the negative lens. As a result, it is possible correct the chromatic aberration favorably.

In a case of exceeding an upper limit value of conditional expression (6), the radius of curvature of the cemented surface becomes excessively large. Consequently, it is not possible to correct the chromatic aberration favorably. Therefore, it is not preferable to exceed the upper limit value of conditional expression (6).

In a case of exceeding an upper limit value of conditional expression (7) is exceeded, the radius of curvature of the image-side surface of the negative lens becomes excessively large. Consequently, it is not possible to achieve the required negative power. Therefore, it is not preferable to exceed the upper limit value of conditional expression (7).

In a case of falling below a lower limit value of conditional expression (7), the radius of curvature of the cemented lens becomes excessively large. Consequently, it is not possible to correct the chromatic aberration favorably. Therefore, it is not preferable to fall below the lower limit value of conditional expression (7).

It is more preferable that the following conditional expression (6') be satisfied instead of conditional expression (6).

$$0 \leq |RCEM/RAf| < 0.02 \quad (6')$$

It is even more preferable that the following conditional expression (6") be satisfied instead of conditional expression (6).

$$0 \leq |RCEM/RAf| < 0.01 \quad (6")$$

It is more preferable that the following conditional expression (7') be satisfied instead of conditional expression (7).

$$-2 < RCEM/RAr < -1 \quad (7')$$

It is even more preferable that the following conditional expression (7") be satisfied instead of conditional expression (7).

$$-1.5 < RCEM/RAr < -1.3 \quad (7")$$

In the endoscope optical system of the present embodiment, it is preferable that the third lens group include a positive lens.

By the positive lens and the cemented lens, it is possible to correct an aberration more favorably. The positive lens may have been disposed on the object side of the cemented lens or on the image side of the cemented lens.

In the endoscope optical system according to the present embodiment, it is preferable that the third lens group include in order from the object side, a positive lens and a predetermined cemented lens, and the predetermined cemented lens includes a positive lens and a negative lens, and the following conditional expressions (8) and (9) are satisfied:

$$10 < D01/DB < 50 \quad (8)$$

$$5 < D02/DB < 20 \quad (9)$$

where,

D01 denotes a thickness on an optical axis of the positive lens in the predetermined cemented lens, D02 denotes a thickness on an optical axis of the negative lens in the predetermined cemented lens, and DB denotes an air space between the positive lens and the predetermined cemented lens.

Conditional expression (8) is a conditional expression in which a ratio of the thickness on the optical axis of the positive lens in the predetermined cemented lens and the air space between the positive lens and the predetermined cemented lens is indicated. Conditional expression (9) is a conditional expression in which a ratio of the thickness on the optical axis of the negative lens in the cemented lens and the air space between the positive lens and the predetermined cemented lens is indicated.

By satisfying conditional expressions (8) and (9), it is possible to make each of the thickness of the positive lens in the predetermined cemented lens and the thickness of the negative lens in the predetermined cemented lens an appropriate thickness, and to make the air space between the positive lens and the predetermined cemented lens an appropriate air space. Consequently, the endoscope optical system is not enlarged in an optical axial direction, and it is possible to make favorable the workability of each lens.

In a case of either falling below a lower limit value of conditional expression (8) or falling below a lower limit value of conditional expression (9), a thickness of each lens becomes excessively thin. In this case, it is not possible to secure an edge thickness of each lens adequately. Therefore, it is not preferable to fall below the lower limit value of conditional expression (8) or to fall below the lower limit value of conditional expression (9).

An annular member for adjusting spacing is disposed between the positive lens and the predetermined cemented lens. In a case of either exceeding an upper limit value of conditional expression (8) or exceeding an upper limit value of conditional expression (9), the air space between the positive lens and the predetermined cemented lens becomes excessively small. In this case, it is not possible to dispose the annular member. Therefore, it is not preferable to exceed the upper limit value of conditional expression (8) and to exceed the upper limit value of conditional expression (9).

It is more preferable that the following conditional expression (8') be satisfied instead of conditional expression (8).

$$15 < D01/DB < 40 \tag{8'}$$

It is even more preferable that the following conditional expression (8") be satisfied instead of conditional expression (8).

$$20 < D01/DB < 35 \tag{8''}$$

It is more preferable that the following conditional expression (9') be satisfied instead of conditional expression (9).

$$6 < D02/DB < 15 \tag{9'}$$

It is even more preferable that the following conditional expression (9") be satisfied instead of conditional expression (9).

$$7 < D02/DB < 11 \tag{9''}$$

In the endoscope optical system according to the present embodiment, it is preferable that the following conditional expression (10) be satisfied:

$$1.01 < \omega\ normal/\omega\ near < 5.0 \tag{10}$$

where,

ω normal denotes a half angle of view at the time of the normal observation, and ω near denotes a half angle of view at the time of the magnified observation.

In the normal observation, it is possible to observe a range wider than a range in the magnified observation. Therefore, the normal observation is carried out to check a lesion part if any. In a case in which a lesion part is detected in the normal observation, the magnified observation of the lesion part is carried out. By doing so, it is possible to observe the lesion part in detail. Moreover, since the detailed observation is possible, it is possible to make a diagnosis with higher accuracy.

Conditional expression (10) is a conditional expression indicating a change in an angle of view of the endoscope optical system. By satisfying conditional expression (10), an observation in a field of view of appropriate width is possible in each of the normal observation and the magnified observation. Particularly, when conditional expression (10) is satisfied, a magnification ratio in the magnified observation becomes large. In this case, since it is possible to move closer to the lesion part, a detailed magnified observation of the lesion part becomes possible.

In a case of falling below a lower limit value of conditional expression (10), a change in the angle of view becomes excessively small. In this case, a difference in a width of a field of view at the time of the normal observation and a width of a field of view at the time of a close observation becomes small. Consequently, it is possible to carry out only one of an observation of a wide range and an observation of a narrow range. In other words, a practical utility of the optical system is lowered.

In a case of exceeding an upper limit value of conditional expression (10), the change in the angle of view becomes excessively large. In this case, since a diameter of lens becomes large, the optical system becomes large in side.

The endoscope optical system of the present embodiment is to be disposed in an insertion portion of endoscope. When the optical system becomes large, a diameter of the insertion portion also becomes thick. When the diameter of the insertion portion becomes thick, a QOL (quality of life), such as a stress on patient at the time of examination increases. Therefore, it is not preferable that the optical system become large in size.

It is more preferable that the following conditional expression (10') be satisfied instead of conditional expression (10).

$$1.03 < \omega\ normal/\omega\ near < 3.0 \tag{10'}$$

It is even more preferable that the following conditional expression (10") be satisfied instead of conditional expression (10).

$$1.04 < \omega\ normal/\omega\ near < 2.0 \tag{10''}$$

In the endoscope optical system of the present embodiment, it is preferable that the predetermined cemented lens be a cemented lens which includes an object-side lens and an image-side lens, and a positive lens is the object-side lens and a negative lens is the image-side lens.

In the endoscope optical system of the present embodiment, it is preferable that the following conditional expressions be satisfied:

$$1.95 < nd01 < 2.00$$

$$1.45 < nd02 < 1.50$$

$70.2 < vd01 < 70.3$ $17.4 < vd02 < 17.5$

Examples will be described below.

EXAMPLE 1

Figure 2A:
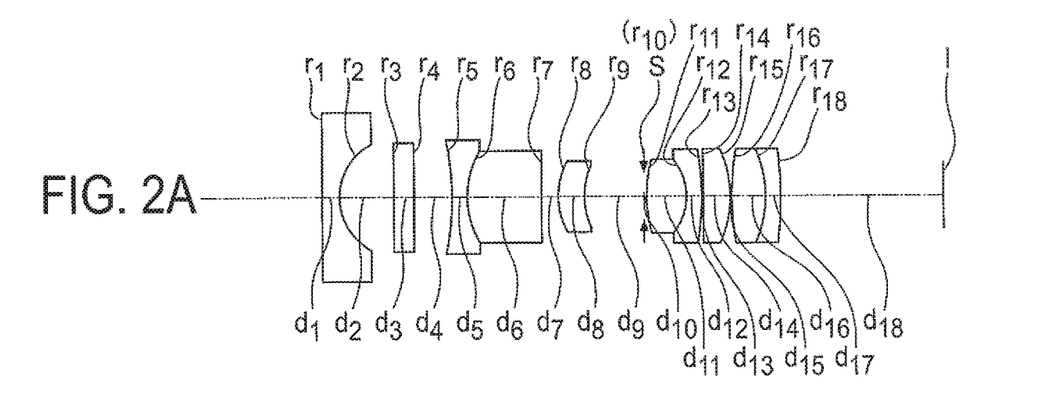
FIG. 2A and FIG. 2B are cross-sectional views of an endoscope optical system according to an example 1.
Figure 2B:
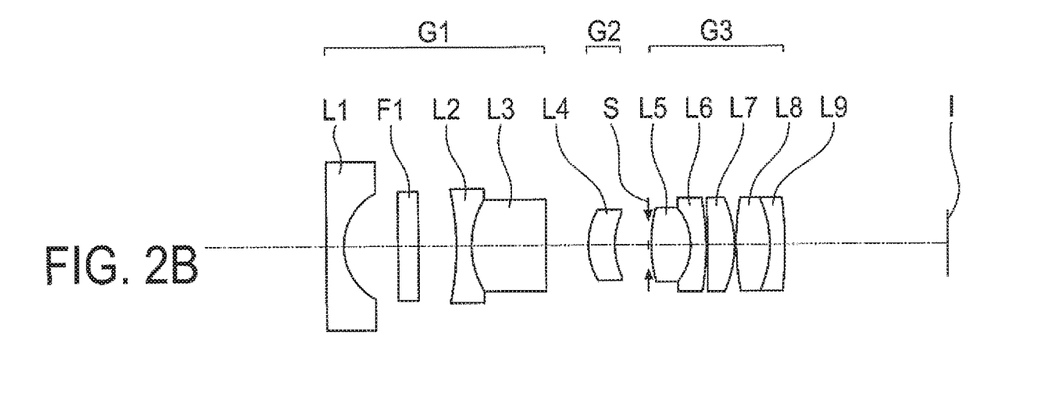
Figure 3A:
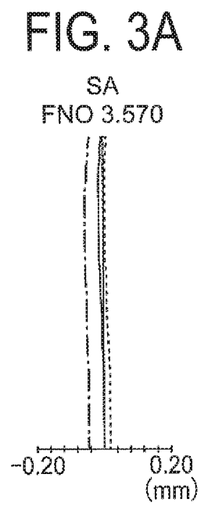
FIG. 3A, FIG. 3B, FIG. 3C, FIG. 3D, FIG. 3E, FIG. 3F, FIG. 3G, and FIG. 3H are aberration diagrams of the endoscope optical system according to the example 1.
Figure 3B:
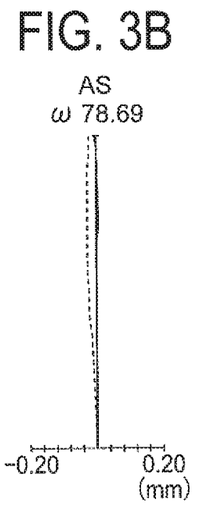
Figure 3C:
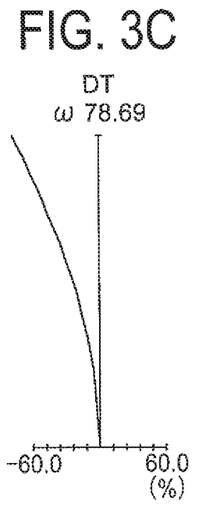
Figure 3D:
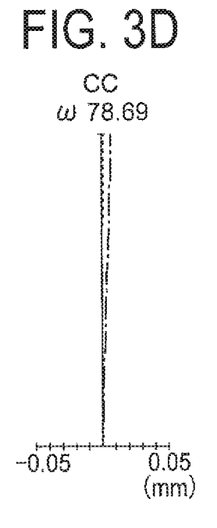
Figure 3E:
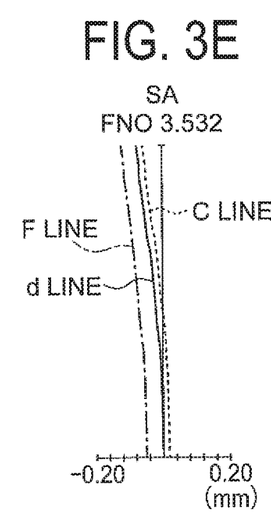
Figure 3F:
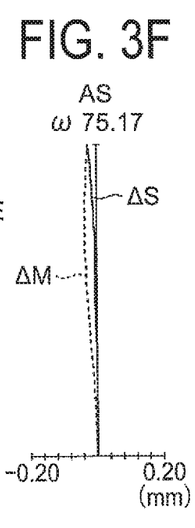
Figure 3G:
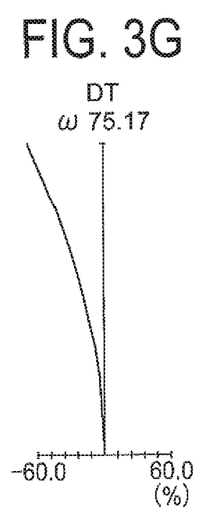
Figure 3H:
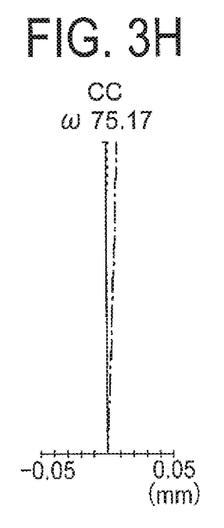

An endoscope optical system according to an example 1 will be described below. FIG. 2A and FIG. 2B are lens cross-sectional views of the endoscope optical system according to the example 1, where, FIG. 2A is a cross-sectional view in a normal observation state and FIG. 2B is a cross-sectional view in a magnified observation state.

The endoscope optical system of the example 1 includes in order from an object side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a planoconvex positive lens L3. Here, the biconcave negative lens L2 and the planoconvex positive lens L3 form a cemented lens.

The second lens group G2 includes a positive meniscus lens L4 having a convex surface directed toward the object side.

The third lens group G3 includes a biconvex positive lens L5, a negative meniscus lens L6 having a convex surface directed toward an image side, a positive meniscus lens L7 having a convex surface directed toward the object side, a biconvex positive lens L8, and a negative meniscus lens L9 having a convex surface directed toward the image side. Here, the biconvex positive lens L5 and the negative meniscus lens L6 form a cemented lens. The biconvex positive lens L8 and the negative meniscus lens L9 form a cemented lens.

An aperture stop S is disposed between the second lens group G2 and the third lens group G3. More precisely, the aperture stop S is disposed near an object-side surface of the biconvex positive lens L5.

A plane parallel plate F1 is disposed on the image side of the planoconcave negative lens L1. The plane parallel plate F1 is an infrared absorbing filter for example.

At the time of switching between the normal observation and the magnified observation, the second lens G2 moves. At the time of switching from the normal observation to the magnified observation, the second lens group G2 moves toward the image side.

FIG. 3A, FIG. 3B, FIG. 3C, and FIG. 3D are aberration diagrams of a spherical aberration (SA), an astigmatism (AS), a distortion (DT), and a chromatic aberration of magnification (CC) respectively, in a normal observation state of the example 1. FIG. 3E, FIG. 3F, FIG. 3G, and FIG. 3H are aberration diagrams of a spherical aberration (SA), an astigmatism (AS), a distortion (DT), and a chromatic aberration of magnification (CC) respectively, in a magnified observation state of the example 1.

In the aberration diagrams, a horizontal axis indicates an amount of aberration. The unit of the amount of aberration is mm for the spherical aberration, the astigmatism, and the chromatic aberration of magnification, and the unit of the amount of aberration for the distortion is %. Moreover, ω denotes a half angle of view and the unit thereof is °, and FNO denotes an F-number. The unit of a wavelength of an aberration curve is nm. Same is true for an example 2.

EXAMPLE 2

Figure 4A:
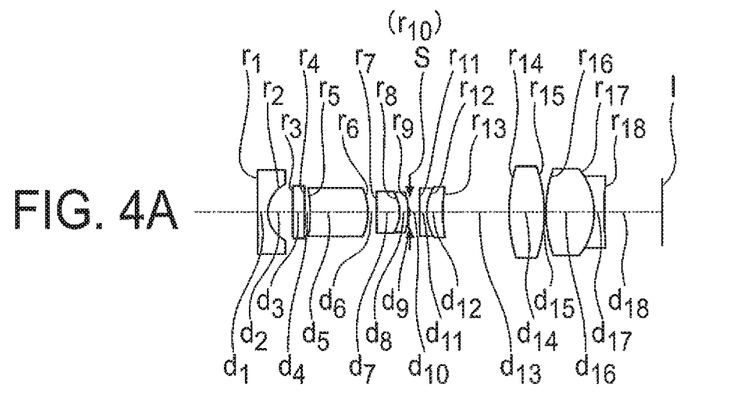
FIG. 4A and FIG. 4B are cross-sectional views of an endoscope optical system according to an example 2.
Figure 4B:
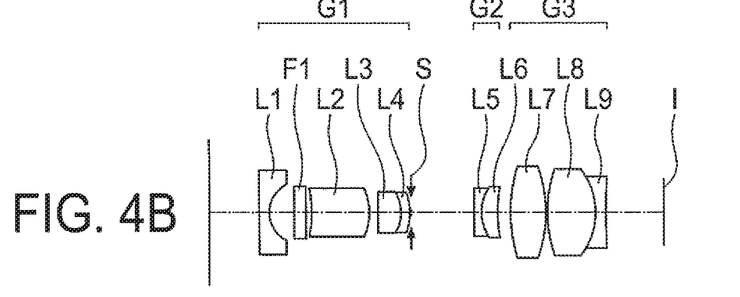
Figure 5A:
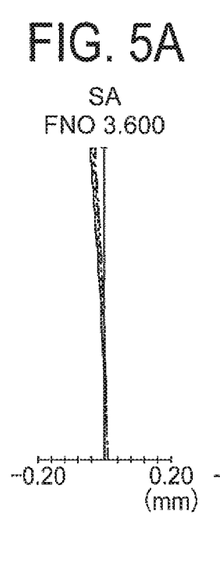
FIG. 5A, FIG. 5B, FIG. 5C, FIG. 5D, FIG. 5E, FIG. 5F, FIG. 5G, and FIG. 5H are aberration diagrams of the endoscope optical system according to the example 2.
Figures 5B, 5C:
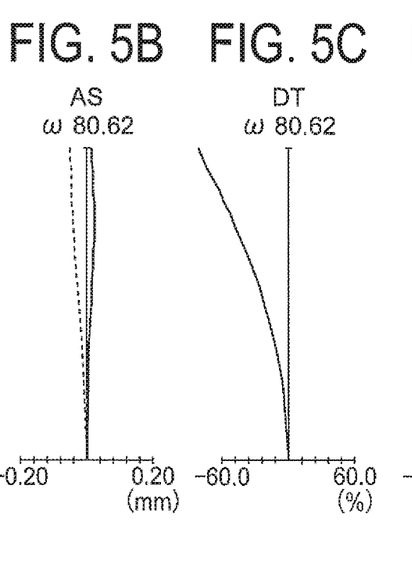
Figure 5D:
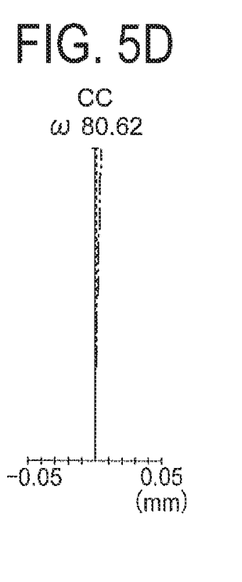
Figure 5E:
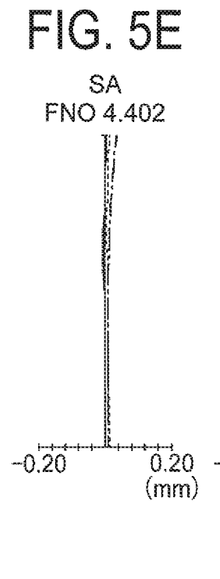
Figure 5F:
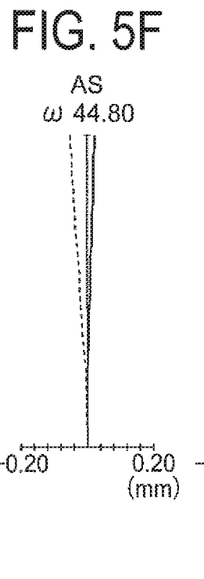
Figure 5G:
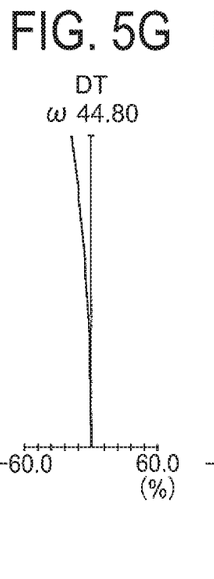
Figure 5H:
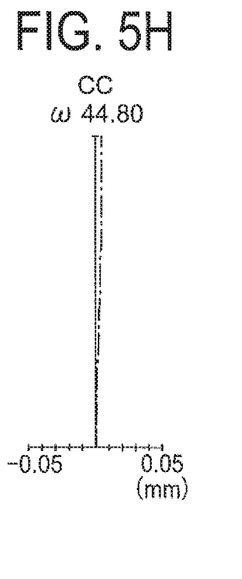

An endoscope optical system according to the example 2 will be described below. FIG. 4A and FIG. 4B are lens cross-sectional views of the endoscope optical system according to the example 2, where, FIG. 4A is a cross-sectional view in a normal observation state and FIG. 4B is a cross-sectional view in a magnified observation state.

The endoscope optical system of the example 2 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a planoconvex positive lens L3, and a negative meniscus lens L4 having a convex surface directed toward the image side. Here, the planoconvex positive lens L3 and the negative meniscus lens L4 form a cemented lens.

The second lens group G2 includes a planoconcave negative lens L5 and a positive meniscus lens L6 having a convex surface directed toward the object side. Here, the planoconcave negative lens L5 and the positive meniscus lens L6 form a cemented lens.

The third lens group G3 includes a biconvex positive lens L7, a biconvex positive lens L8, and a biconcave negative lens L9. Here, the biconvex positive lens L8 and the biconcave negative lens L9 form a cemented lens.

An aperture stop S is disposed between the first lens group G1 and the second lens group G2. More precisely, the aperture stop S is disposed near an image-side surface of the negative meniscus lens L4.

A plane parallel plate F1 is disposed on the image side of the planoconcave negative lens L1. The plane parallel plate F1 is an infrared absorbing filter for example.

At the time of switching between the normal observation and the magnified observation, the second lens group G2 moves. At the time of switching from the normal observation to the magnified observation, the second lens group G2 moves toward the image side.

FIG. 5A, FIG. 5B, FIG. 5C, and FIG. 5D are aberration diagrams of a spherical aberration (SA), an astigmatism (AS), a distortion (DT), and a chromatic aberration of magnification (CC) respectively, in a normal observation state of the example 2. FIG. 5E, FIG. 5F, FIG. 5G, and FIG. 5H are aberration diagrams of a spherical aberration (SA), an astigmatism (AS), a distortion (DT), and a chromatic aberration of magnification (CC) respectively, in a magnified observation state of the example 2.

Numerical data of each example described above is shown below. In Surface data, in symbols, r denotes radius of curvature of each lens surface, d denotes a distance between respective lens surfaces, nd denotes a refractive index of each lens for a d-line, vd denotes an Abbe number for each lens.

In various data, f denotes a focal length in d-line, FNO. denotes an F number, and ω denotes a half angle of view.

EXAMPLE 1

| Unit mm | | | | |
|---|---|---|---|---|
| Surface data | | | | |
| Surface no. | r | d | nd | vd |
| 1 | ∞ | 0.53 | 1.88300 | 40.76 |
| 2 | 1.800 | 1.65 | | |

-continued

Unit mm

| | | | | |
|---|---|---|---|---|
| 3 | ∞ | 0.61 | 1.52100 | 65.12 |
| 4 | ∞ | 1.15 | | |
| 5 | −8.042 | 0.45 | 1.88300 | 40.76 |
| 6 | 2.669 | 2.27 | 1.84666 | 23.78 |
| 7 | ∞ | 0.05 | | |
| 8 | ∞ | Variable | | |
| 9 | 2.185 | 0.80 | 1.48749 | 70.23 |
| 10 | 2.272 | 0.83 | | |
| 11 | ∞ | Variable | | |
| 12(Stop) | ∞ | 0.08 | | |
| 13 | 4.335 | 1.18 | 1.67270 | 32.10 |
| 14 | −1.766 | 0.45 | 2.00330 | 28.27 |
| 15 | −8.149 | 0.05 | | |
| 16 | −72.358 | 0.83 | 1.69895 | 30.13 |
| 17 | −3.415 | 0.05 | | |
| 18 | 8.082 | 1.01 | 1.48749 | 70.23 |
| 19 | −3.427 | 0.45 | 1.95906 | 17.47 |
| 20 | −11.590 | 4.96 | | |
| Imaging surface | ∞ | | | |

Various data

| | Normal observation state | magnified observation state |
|---|---|---|
| f | 1.02 | 1.03 |
| FNO. | 3.57 | 3.53 |
| 2ω | 158.57 | 151.29 |
| d8 | 0.45 | 1.24 |
| d11 | 0.97 | 0.18 |

Unit focal length

| f1 = −1.23 | f2 = 28.99 | f3 = 3.64 |
|---|---|---|

EXAMPLE 2

Unit mm

Surface data

| Surface no. | r | d | nd | vd |
|---|---|---|---|---|
| 1 | ∞ | 0.30 | 1.88300 | 40.76 |
| 2 | 0.942 | 0.74 | | |
| 3 | ∞ | 0.35 | 1.52100 | 65.12 |
| 4 | ∞ | 0.17 | | |
| 5 | −4.022 | 1.72 | 1.58144 | 40.75 |
| 6 | −1.766 | 0.26 | | |
| 7 | ∞ | 0.70 | 1.53172 | 48.84 |
| 8 | −1.151 | 0.26 | 1.92286 | 18.90 |
| 9 | −1.825 | 0.04 | | |
| 10(Stop) | ∞ | 0.03 | | |
| 11 | ∞ | Variable | | |
| 12 | ∞ | 0.22 | 1.77250 | 49.60 |
| 13 | 1.352 | 0.48 | 1.69895 | 30.13 |
| 14 | 4.178 | 0.09 | | |
| 15 | ∞ | Variable | | |
| 16 | 4.753 | 1.04 | 1.81600 | 46.62 |
| 17 | −4.040 | 0.04 | | |
| 18 | 3.956 | 1.44 | 1.48749 | 70.23 |
| 19 | −2.089 | 0.30 | 1.95906 | 17.47 |
| 20 | 15.196 | 1.73 | | |
| Imaging surface | ∞ | | | |

Various data

| | Normal observation state | magnified observation state |
|---|---|---|
| f | 0.97 | 1.19 |
| FNO. | 3.60 | 4.40 |
| 2ω | 161.83 | 89.79 |
| d11 | 0.27 | 1.87 |
| d15 | 1.90 | 0.30 |

Unit focal length

| f1 = 1.79 | f2 = −4.46 | f3 = 2.94 |
|---|---|---|

The values of conditional expressions (1) to (10) according to the first example and second example are shown below.

| Conditional Expression | Example1 | Example2 |
|---|---|---|
| (1)nd02 − nd01 | 0.472 | 0.472 |
| (2)vd01 − vd02 | 52.760 | 52.760 |
| (3)(nd02 − nd01)/fno | 0.132 | 0.131 |
| (4)nd01/ndA | 0.790 | 0.790 |
| (5)nd02/ndA | 1.0404 | 1.0404 |
| (6)|RCEM/RAf| | 0.000 | 0.000 |
| (7)RCEM/RAr | −1.904 | −2.218 |
| (8)D01/DB | 22.375 | 33.011 |
| (9)D02/DB | 10.020 | 7.002 |
| (10)ωnormal/ωnear | 1.048 | 1.802 |

The values of parameters are shown below.

| parameter | Example1 | Example2 |
|---|---|---|
| nd01 | 1.48749 | 1.48749 |
| nd02 | 1.95906 | 1.95906 |
| vd01 | 70.23 | 70.23 |
| vd02 | 17.47 | 17.47 |
| fno | 3.57 | 3.6 |
| ndA | 1.883 | 1.883 |
| RCEM | −3.4267 | −2.0888 |
| RAf | ∞ | ∞ |
| RAr | 1.7996 | 0.9417 |
| D01 | 1.0136 | 1.436 |
| D02 | 0.4539 | 0.3046 |
| DB | 0.0453 | 0.0435 |

According to each example, it is possible to provide an endoscope optical system in which switching between the normal observation and magnified observation is possible, and the chromatic aberration is corrected favorably.

Various embodiments of the present invention have been described heretofore. However, the present invention is not restricted to the embodiments described, and embodiments in which the arrangements of the embodiments are combined appropriately without departing from the scope of the present invention are also in the category of the present invention.

The present embodiment enables to provide an endoscope optical system in which, switching between the normal observation and the magnified observation is possible, and a chromatic aberration is corrected favorably.

As described heretofore, the present invention is suitable for an endoscope optical system in which switching between the normal observation state and the magnified observation state is possible, and the chromatic aberration is corrected favorably.

What is claimed is:

1. An endoscope optical system comprising, in order from an object side:
   a first lens group having a negative refractive power;
   a second lens group having a positive refractive power; and
   a third lens group having a positive refractive power, wherein:
   switching between a normal observation and a magnified observation is possible by fixing the first lens group and the third lens group, and moving the second lens group,
   the third lens group includes a cemented lens,
   the cemented lens includes an object-side lens and an image-side lens, and
   the following conditional expressions (1), (2), and (3) are satisfied:

$$0.471 < nd02 - nd01 < 0.475 \quad (1)$$

$$52.6 < vd01 - vd02 < 53 \quad (2)$$

$$0.1 < (nd02 - nd01)/fno < 0.2 \quad (3)$$

where,
   nd01 denotes a refractive index of the object-side lens for a d-line,
   nd02 denotes a refractive index of the image-side lens for the d-line,
   vd01 denotes Abbe number for the object-side lens for the d-line,
   vd02 denotes Abbe number for the image-side lens for the d-line, and
   fno denotes an F-number of the endoscope optical system at a time of the normal observation.

2. The endoscope optical system according to claim 1, wherein:
   the first lens group includes a negative lens which is nearest to object, and
   the following conditional expressions (4) and (5) are satisfied:

$$0.76 < nd01/ndA < 0.81 \quad (4)$$

$$1.02 < nd02/ndA < 1.07 \quad (5)$$

where,
   nd01 denotes the refractive index of the object-side lens for the d-line,
   nd02 denotes the refractive index of the image-side lens for the d-line, and
   ndA denotes a refractive index of the negative lens for the d-line.

3. The endoscope optical system according to claim 1, wherein:
   the first lens group includes a negative lens which is nearest to object, and
   the following conditional expressions (6) and (7) are satisfied:

$$0 \geq |RCEM/RAf| < 0.03 \quad (6)$$

$$-5 < RCEM/RAr < -0.5 \quad (7)$$

where,
   RAf denotes a radius of curvature of an object-side surface of the negative lens,
   RAr denotes a radius of curvature of an image-side surface of the negative lens, and
   RCEM denotes a radius of curvature of a cemented surface of the cemented lens.

4. The endoscope optical system according to claim 1, wherein:
   the third lens group includes, in order from the object side, a positive lens and the cemented lens,
   the cemented lens includes, as the object-side lens and the image-side lens, a positive lens and a negative lens, respectively, and
   the following conditional expressions (8) and (9) are satisfied:

$$10 < D01/DB < 50 \quad (8)$$

$$5 < D02/DB < 20 \quad (9)$$

where,
   D01 denotes a thickness on an optical axis of the positive lens in the cemented lens,
   D02 denotes a thickness on the optical axis of the negative lens in the cemented lens, and
   DB denotes an air space between the positive lens and the cemented lens.

5. The endoscope optical system according to claim 1, wherein the following conditional expression (10) is satisfied:

$$1.01 < \omega \text{ normal}/\omega \text{ near} < 5.0 \quad (10)$$

where,
   $\omega$ normal denotes a half angle of view at the time of the normal observation, and
   $\omega$ near denotes a half angle of view at a time of the magnified observation.

6. An image pick-up apparatus comprising:
   the endoscope optical system according to claim 1.

7. An endoscope comprising:
   the endoscope optical system according to claim 1.

8. An endoscope optical system comprising, in order from an object side:
   a first lens group having a negative refractive power;
   a second lens group having a positive refractive power; and
   a third lens group having a positive refractive power, wherein:
   switching between a normal observation and a magnified observation is possible by fixing the first lens group and the third lens group, and moving the second lens group,
   the third lens group includes, in order from the object side, a positive lens and a cemented lens,
   the cemented lens includes a positive object-side lens and a negative image-side lens, and
   the following conditional expressions (1), (2), (8), and (9) are satisfied:

$$0.471 < nd02 - nd01 < 0.475 \quad (1)$$

$$52.6 < vd01 - vd02 < 53 \quad (2)$$

$$10 < D01/DB < 50 \quad (8)$$

$$5 < D02/DB < 20 \quad (9)$$

where,
   nd01 denotes a refractive index of the object-side lens for a d-line,
   nd02 denotes a refractive index of the image-side lens for the d-line,
   vd01 denotes Abbe number for the object-side lens for the d-line,
   vd02 denotes Abbe number for the image-side lens for the d-line, D01 denotes a thickness on an optical axis of the object-side lens, D02 denotes a thickness on the optical axis of the image-side lens, and DB denotes an air space between the positive lens and the cemented lens.

9. The endoscope optical system according to claim 8, wherein:

the first lens group includes a negative lens which is nearest to object, and the following conditional expressions (4) and (5) are satisfied:

$$0.76 < nd01/ndA < 0.81 \quad (4)$$

$$1.02 < nd02/ndA < 1.07 \quad (5)$$

where, nd01 denotes the refractive index of the object-side lens for the d-line, nd02 denotes the refractive index of the image-side lens for the d-line, and ndA denotes a refractive index of the negative lens for the d-line.

10. The endoscope optical system according to claim 8, wherein:

the first lens group includes a negative lens which is nearest to object, and the following conditional expressions (6) and (7) are satisfied:

$$0 \leq |RCEM/RAf| < 0.03 \quad (6)$$

$$-5 < RCEM/RAr < -0.5 \quad (7)$$

where,

RAf denotes a radius of curvature of an object-side surface of the negative lens, RAr denotes a radius of curvature of an image-side surface of the negative lens, and RCEM denotes a radius of curvature of a cemented surface of the cemented lens.

11. The endoscope optical system according to claim 8, wherein the following conditional expression (10) is satisfied:

$$1.01 < \omega\ normal/\omega\ near < 5.0 \quad (10)$$

where,

ω normal denotes a half angle of view at the time of the normal observation, and ω near denotes a half angle of view at a time of the magnified observation.

12. An image pick-up apparatus comprising:
the endoscope optical system according to claim 8.

13. An endoscope comprising:
the endoscope optical system according to claim 8.

14. An endoscope optical system comprising, in order from an object side:

a first lens group having a negative refractive power;

a second lens group having a positive refractive power; and a third lens group having a positive refractive power, wherein:

switching between a normal observation and a magnified observation is possible by fixing the first lens group and the third lens group, and moving the second lens group, the first lens group includes all of lenses positioned on an object side of the second lens group, the third lens group includes all of lenses positioned on an image side of the second lens group, the third lens group includes a cemented lens, the cemented lens includes an object-side lens and an image-side lens, and the following conditional expressions (1) and (2) are satisfied:

$$0.471 < nd02 - nd01 < 0.475 \quad (1)$$

$$52.6 < vd01 - vd02 < 53 \quad (2)$$

where, nd01 denotes a refractive index of the object-side lens for a d-line, nd02 denotes a refractive index of the image-side lens for the d-line, vd01 denotes Abbe number for the object-side lens for the d-line, and vd02 denotes Abbe number for the image-side lens for the d-line.

\* \* \* \* \*